United States Patent [19]
Sodickson et al.

[11] Patent Number: 5,818,048
[45] Date of Patent: Oct. 6, 1998

[54] RAPID NON-INVASIVE OPTICAL ANALYSIS USING BROAD BANDPASS SPECTRAL PROCESSING

[75] Inventors: Lester Sodickson, Waban; Howard E. Guthermann, Newton, both of Mass.; Myron J. Block, North Salem, N.H.

[73] Assignee: Optix LP, Jensen Beach, Fla.

[21] Appl. No.: 333,758

[22] Filed: Nov. 3, 1994

Related U.S. Application Data

[63] Continuation-in-part of Ser. No. 130,257, Oct. 1, 1993, Pat. No. 5,434,412, Ser. No. 182,572, Jan. 14, 1994, Pat. No. 5,424,545, and Ser. No. 207,871, Mar. 8, 1994, abandoned, which is a division of Ser. No. 914,265, Jul. 15, 1992, Pat. No. 5,321,265.

[51] Int. Cl.$^6$ .................................................. G01N 21/35
[52] U.S. Cl. ................................. 250/343; 356/405
[58] Field of Search ..................... 250/343, 339.01, 250/340, 341.1, 345; 356/405

[56] References Cited

U.S. PATENT DOCUMENTS

| | | | |
|---|---|---|---|
| 4,178,917 | 12/1979 | Shapiro | 128/665 |
| 4,278,538 | 7/1981 | Lawrence et al. | 209/580 |
| 4,286,327 | 8/1981 | Rosenthal et al. | 364/498 |
| 4,520,265 | 5/1985 | Griggs et al. | 250/338 |
| 4,543,481 | 9/1985 | Zwick | 250/339 |
| 4,641,973 | 2/1987 | Nestler et al. | 356/418 |
| 4,655,225 | 4/1987 | Dähne et al. | 128/633 |
| 4,799,795 | 1/1989 | Fateley | 356/310 |
| 4,805,623 | 2/1989 | Jöbsis | 250/339.12 |
| 4,850,365 | 7/1989 | Rosenthal | 128/664 |
| 4,882,492 | 11/1989 | Schlager | 250/346 |
| 4,883,953 | 11/1989 | Koashi et al. | 250/226 |
| 4,928,014 | 5/1990 | Rosenthal | 250/341 |
| 4,975,581 | 12/1990 | Robinson et al. | 250/339 |
| 5,028,787 | 7/1991 | Rosenthal et al. | 250/341 |
| 5,054,487 | 10/1991 | Clarke | 128/633 |
| 5,070,874 | 12/1991 | Barnes et al. | 128/633 |
| 5,321,265 | 6/1994 | Block | 250/343 |
| 5,321,565 | 6/1994 | Shibaike et al. | 360/85 |

FOREIGN PATENT DOCUMENTS

| | | |
|---|---|---|
| 0 030 610 | 6/1981 | European Pat. Off. . |
| 0233873 | 3/1986 | Germany . |
| 1187032 | 11/1985 | U.S.S.R. . |
| WO 88/01128 | 2/1988 | WIPO . |

OTHER PUBLICATIONS

Moore et al. (1991) "Real–Time Neural System for Color Constancy" Abstract, *IEEE Transactions on Neural Networks*, 2(2):237.

Polish et al. (1992) "Noscomial Transmission of Hepatitis B Virus Associated With the Use of a Spring–Loaded Finger–Stick Device" *New England Journal of Medicine* 326(11):721–725.

(List continued on next page.)

*Primary Examiner*—Michael J. Tokar
*Assistant Examiner*—Richard Hanig
*Attorney, Agent, or Firm*—Lahive & Cockfield, LLP

[57] ABSTRACT

The present invention provides a generally applicable apparatus and method for achieving measurements of a constituent in a sample. This is achieved by employing a detection means having a plurality of detectors responsive to radiation in a selected region of the spectrum, e.g., the infrared. In most embodiments, at least two of the detectors provide broad wavelength bandpass. If narrow bandpass sources or detectors are used, the information generated is processed in a manner similar to broadband information. The broad bandpass response of the detectors can be contrasted with the approach of classical spectrophotometry, in which the spectral response of the detectors is designed to be as narrow as feasible, and substantially narrower than the spectral features of the constituent or constituents of interest. The data is processed such that the contributions of known background constituents and scattering is eliminated prior to further processing, thereby yielding a better result in high background situations. The use of intensity processing rather than absorbance processing also allows the method and apparatus to be used in a variety of non-ideal situations.

64 Claims, 12 Drawing Sheets

OTHER PUBLICATIONS

Rubner and Schulther (1989) "A Regular Approach to Color Constancy" *Bio Cybern* 65:29–36.

Schmitt (1991) "Simple Photon Diffusion Analysis of the Effects of Multiple Scattering on Pulse Oximetry" Abstract, *IEEE Transaction on Biomedical Engineering,* 38(12):1194.

Willard et al. (1981) "Instrumental Methods of Analysis" 6th ed. (NY: D. Van Nostrand Co.) 58, 76, 852, 853.

Wukitsch et al. (1988) "Pulse Oximeter: Analysis of Theory, Technology, and Practice" *J. Clin. Monit.,* 4: 290–301.

Bohlke et al. (1991) "A new stationary Hadamard encoding masks for near–infrared Hadamard transform Raman spectrometry" *Journal of Molecular Structure* 247: 293–303.

Cavinato et al. (1990) "Noninvasive Method for Monitoring Ethanol in Fermentation Processes Using Fiber–Optic Near–Infrared Spectroscopy" *Anal. Chem.* 62: 1977–1982.

Dufort and Lumsden (1991) "Color categorization and color constancy in neutral network model of V4" *Biol. Cybern.* 65: 293–303.

Dyer et al. (1989) "A Fast Spectrum–Recovery Method for Hadamard Transform Spectrometers Having Nonideal Masks" *Applied Spectroscopy* 43(3):435–440.

RAPID NON-INVASIVE OPTICAL ANALYSIS USING BROAD BANDPASS SPECTRAL PROCESSING

REFERENCE TO RELATED APPLICATIONS

This application is a Continuation-in-Part of U.S. patent application Ser. No. 207,871, filed Mar. 8, 1994, now abandoned entitled "Non-invasive Testing", which is a divisional of 07/914,265, filed Jul. 15, 1992, U.S. Pat. No. 5,321,265, also entitled "Non-invasive Testing". This application is also a Continuation-in-Part of U.S. patent application Ser. No. 130,257, entitled: "Improvements in Non-Spectrophotometric Measurement of Analyte Concentrations and Optical Properties of Objects," filed Oct. 1, 1993 now U.S. Pat. No. 5,434,412; and U.S. patent application Ser. No. 182,572, filed Jan. 14, 1994, entitled "Non-Invasive Non-Spectrophotometric Infrared Measurement of Blood Analyte Concentrations"now U.S. Pat. No. 5,424,545. The disclosures of all these applications are incorporated herein by reference.

BACKGROUND OF THE INVENTION

The present invention relates to the measurement of the concentration of constituents or other properties of interest of a material using radiation, preferably near infrared radiation. More particularly, apparatus and methods have been developed for measurement of the concentration of constituents such as hemoglobin and its variants and derivatives, glucose, cholesterol and its combined forms, drugs of abuse, and other analytes of clinical and diagnostic significance in a non-invasive manner. Because the apparatus developed for use of this method does not require the withdrawal of blood in order to perform these measurements, it is particularly suitable for testing in the home on a chronic basis, such as for glucose levels in diabetics and for kidney function, e.g., urea or creatinine testing, in patients undergoing home dialysis.

In addition to home testing, development of clinical testing procedures that do not require blood withdrawal has become an important goal, due to the spread of AIDS and the associated fears among the public and health care personnel. Along with AIDS, other diseases such as hepatitis can be spread through the use of invasive procedures without stringent precautions to assure sterility. A recent article, "Nosocomial transmission of hepatitis B virus associated with the use of a spring-loaded finger-stick device," *New England Journal of Medicine*, 326(11), 721–725 (1992), disclosed a hepatitis mini-epidemic in a hospital caused by the improper use of an instrument for obtaining blood samples. The article describes how the hospital personnel unintentionally transmitted the virus from patient to patient by misuse of the sampling device. Such transfers, potentially hazardous to healthcare personnel as well as patients, are eliminated by non-invasive testing such as that performed by the subject apparatus and methods.

Non-invasive testing will become particularly effective in the long-term management of diabetes. Improperly controlled glucose levels in diabetes patients can result in damage to the circulatory system, the nervous system, the retina, and other organs. These damages can be largely eliminated by closer control of glucose levels on a daily basis. However, this closer control requires measurement of glucose levels four or more times a day. With current apparatus and methods, a painful finger prick is required for each sample. Furthermore, the part of the apparatus that contacts the blood to produce the required chemical change used in the measurement is disposed of after each sample. The cost to the user of these disposables can reach thousands of dollars per year. The inconvenience and discomfort of the sampling adds to the psychic costs of the process. Finally, the sampling process, conducted by relatively untrained personnel, has been reported to multiply the inherent error in the analytical process by a factor of three to five times. Errors in the sampling process occur as a result of not obtaining a proper blood sample (e.g., the sample may be an admixture of intracellular fluid with the blood sample) and as a result of improper application of the sample to the disposable part of the apparatus.

These deficiencies in currently available apparatus and methods have caused a number of groups to attempt to develop non-invasive apparatus for measurement of concentration of various constituents of blood. Commercially, the most successful apparatus for non-invasive chemical constituent measurements are those for "pulse oximetry", where the apparatus is used to measure relative concentrations of oxyhemoglobin and deoxyhemoglobin. These are both strong absorbers in the near infrared, with crossing broadband features, so ratioing of intensities of radiation at two wavelengths can provide the requisite information. Based in part on the success with hemoglobin, much of the current work on non-invasive measurements for chemical constituents has also used the near-infrared region of the electromagnetic spectrum. Because of the large size of the glucose market, most of the additional research is directed to glucose although it is only a low concentration material with weak absorbance. The region from 700 to 1100 nm in wavelength contains the third overtones of the glucose spectrum, theoretically allows minimization of interferences due to water absorption, and exhibits good penetration of human tissue. Other promising research has used longer wavelengths, from 1100 to about 2500 nm.

Substantially all of this work has been carried out using variants on classic spectrophotometric methods. Such methods typically use detectors which measure the radiation transmitted through or reflected from the sample in relatively narrow wavelength bandpasses. The width of the passband is kept narrow for several theoretical reasons. First, a narrower passband minimizes the practical deviations that can occur relative to the theoretical relationships between constituent concentration and absorbance. Second, measurement with a narrow detector passband allows a better measurement of sharply peaked spectra by providing a measurement closer to the radiation peak. This has been believed to improve specificity, and for full-spectrum measurements, provide a more faithful rendition of the absorbance or reflectance spectrum.

The wavelength passband within which the detector operates can be a property of the source or can be obtained by appropriate filtering means placed between source and sample, between sample and detector, or both. The width of the passband in classic spectrophotometric apparatus is ordinarily chosen to be small with respect to the width of the spectral features of the constituent of interest and the sample, if known. Typically, a passband halfwidth less than 10% of the spectral halfwidth is recommended.

In some apparatus and methods, the source is designed to scan the spectral region of interest, so that the measured wavelength varies over time in a controlled manner. In other cases, the source is transformed into a coded broadband source, whose interaction with the sample is later decomposed into narrow-band responses.

In most of the classic spectrophotometric apparatus and methods, the resultant data initially appear within the apparatus as uncorrected intensity versus wavelength data for the sample. The next important step, performed within the spectrophotometric apparatus, is a logarithmic conversion of the data into absorbance or reflectance units using some reference intensity versus wavelength data for normalization. Extensive data processing of the transformed data is then employed to attempt to isolate the components of the data arising from the constituent(s) of interest and the components arising from the background (due to constituents that are not of interest and instrumental artifacts). A multitude of techniques are employed to perform this isolation, largely based on statistical regression techniques. Examples of this general approach include the work of Rosenthal et al., U.S. Pat. No. 5,028,787 and Clarke, U.S. Pat. No. 5,054,487.

All of these classic methods essentially search for a unique response or pattern of responses due to the constituent of interest at one or more specific wavelengths (or narrow wavelength passbands) and then attempt to separate these effects from the effects due to background constituents at the same narrow wavelength passbands. However, glucose and many other constituents of interest possess only weak broadband spectral features in the wavelength ranges of interest. Furthermore, the measurement environment is generally a mixture containing many constituents with overlapping but different broadband spectral structures, several of which, including water and hemoglobin, are strong absorbers in the region. In non-invasive clinical measurements, the problems are compounded by the presence of multiple diffuse radiation scattering centers in the tissue. These situations are contrary to the basic assumptions of spectrophotometry, and its apparatus and methods are ill-suited to dealing with the resultant data.

Spectra with weak, low resolution features and overlapping backgrounds are, however, commonly found in examination of colored objects by reflected, emitted, or transmitted light in the visible wavelength range. The human eye can distinguish wavelength shifts as small as 2 nm, and can distinguish small wavelength shifts even under variable illumination conditions. Therefore, the present invention is based on concepts analogous to those employed in the human visual system and in colorimetric apparatus.

In apparatus for measuring color (as opposed to concentration), two methods are commonly employed. Traditional (tristimulus) colorimetry employs three detectors with spectral responses approximating those of the visual cones in the human eye (shown in FIG. 1a, the CIE Standard Observer) to create an apparatus with spectral sensitivity approximating that of the eye. To improve the approximation, newer devices employ sets of narrow-band detectors to measure the entire visual spectrum at substantially constant sensitivity and then apply software algorithms to simulate the color response of the eye. In both cases, resultant outputs may be transformed by convolving the Standard Observer response with the known spectra of the source to generate data representative of the color of the object being measured.

Data obtained by these colorimetric devices are often presented in transformed co-ordinate spaces for easier interpretation. Examples of such spaces are shown in FIGS. 1b and c. FIG. 1b is the CIE chromaticity coordinate system, while FIG. 1c is the CIE Lab coordinate system. Results presented in these systems are interpretable as hues, chromas, saturations, brightnesses, and other related terms that are more easily related to human perceptions without further mathematical transformation. The CIE Lab system attempts to create a coordinate space that is linear with perceived color differences. These systems have been used in the reflectance or transmittance mode to measure the color of a reflective or transmissive sample. None of these systems has been used to directly measure the concentration of a constituent or constituents of a sample.

U.S. Pat. No. 5,321,265, the disclosure of which is incorporated herein by reference, discloses a basic concept for creating a system analogous to human color perception and to colorimetry using infrared sources and appropriate detection means for measuring the concentration of constituents of a sample. Briefly, the disclosed methods and apparatus use a broadband radiation source to illuminate a sample held in a chamber. Radiation from the source is passed through a plurality of spectrally overlapping filters before reaching detection means which detect radiation transmitted, reflected or emitted from the sample and thereby measure the sample's "color" in the region of the spectrum defined by the filter and detector responses. U.S. patent applications Ser. Nos. 130,257 and 182,572 concern modifications to the basic apparatus and methods to achieve better results. The present invention concerns further methods and apparatus which may be employed toward the same objective. These methods and apparatus are all directed to improving the accuracy, sensitivity and repeatability of non-invasive measurements of materials such as glucose. The present invention, however, is not limited to overlapping detectors, although it is preferable that at least some of the detectors overlap. Similarly, while broadband detectors are preferred, it is possible to use some, or all, narrow band sources or detectors.

Accordingly, an object of the invention is to provide an apparatus for obtaining a non-invasive measure of the concentration of a constituent of interest using the infrared portion of the spectrum.

A further object of the invention is to provide methods for obtaining a measure of the concentrations in blood or in tissue of clinically important analytes in a non-invasive manner.

These and other objects and features of the invention are achieved by the methods and apparatus described in the Summary of the Invention, the Detailed Description and the Drawing.

SUMMARY OF THE INVENTION

The present invention features new apparatus and methods for measurement of the concentration of a constituent of interest in a sample without withdrawing the sample from its normal environment. The apparatus and methods also have utility in determining the optical properties of objects. The apparatus and methods are generally intended to be used with radiation, preferably between 700—2500 nm, transmitted through or reflected from the object or sample of interest, particularly in the near infrared.

U.S. Pat. No. 5,321,565 discloses an apparatus and method which employ an analog of color vision in the near infrared region of the electromagnetic spectrum to provide improved non-invasive measurements of concentrations of constituents in a sample. The basic concept is that the use of a plurality of broadband spectrally overlapping detectors to measure the radiation transmitted, reflected, or emitted in response to broadband illumination of a sample would result in an analog of color vision, and could generate useful data in situations where other combinations of illumination and detectors could not generate useful data. The spectral response of the detectors can be defined by physical properties of the detectors themselves, or by combinations of detectors with broader spectral responses with appropriately chosen filters to create the required spectral response. The previously cited patent applications provide variations on the methods and apparatus which improve the response of the system.

The present invention provides a more generally applicable apparatus and method for achieving measurements of a constituent in a sample. This is achieved by employing a detection means having a plurality of detectors responsive to radiation in a selected region of the spectrum, e.g., the infrared. In most embodiments, at least two of the detectors provide broad wavelength bandpass. If narrow bandpass sources or detectors are used, the information generated is processed in a manner similar to broadband information. The broad bandpass response of the detectors can be contrasted with the approach of classical spectrophotometry, in which the spectral response of the detectors is designed to be as narrow as feasible, and substantially narrower than the spectral features of the constituent or constituents of interest. For most constituents of interest such as glucose, the detectors bandpass width is broader than the individual identifying spectral characteristics of the constituent of interest.

In classic spectrophotometry, the width of the passband is kept narrow for several reasons. First, a narrower passband minimizes the practical deviations that can occur relative to the theoretical relationships between constituent concentration and absorbance. Beer's law, which linearly relates absorbance and concentration, is inaccurate if too broad a bandwidth is selected. Second, measurement with a narrow detector passband allows a better measurement of sharply peaked spectra by providing a measurement closer to the radiation peak. This usually improves specificity, and for full absorbance spectrum measurements, provides a more faithful rendition of the spectrum. In return for these advantages, however, narrow passband detection suffers from lower signal, so the signal to noise ratios for a given apparatus configuration can be too low to provide meaningful data on low concentration constituents. In the in vivo measuring environment, where the analyte, sample, and background spectra are broad, and the absorption due to trace analytes is low relative to the background, the advantages of narrow bandpass detectors become less important, while the suboptimal S/N behavior becomes critical. In fact, Beer's law does not apply to scattering media such as is found in an in vivo environment, since it was developed for solutions without scattering centers. In contrast, the present invention preferably uses broad bandpass detectors, combined with precomputational processing techniques to maintain S/N ratios. The term "broad bandpass" can be expressed in terms of the halfwidths of relevant sample, constituent, or background spectra, as well as a variety of other factors. Narrow bandpass detectors and/or sources are commonly thought to be required in spectrophotometry for purposes of maintaining adequate linearity and/or specificity. Generally, spectrophotometric systems employ bandpasses under 20 nm in order to achieve these objectives. The present invention relies, rather, on the improved signal obtained from broad bandpass detectors and sources to provide more optimum signal to noise ratios. If narrow bandpass filters are used in the present invention, their use is permitted if the features being observed are broad, if no sharp anomaly in the spectrum is observed in the area under investigation, and if the S/N ratio for the associated detector remains adequate. In such cases, the narrow bandpass detector outputs are treated as if they were generated by broad bandpass detectors.

FIG. 2 compares the spectral response from the various embodiments of the present invention, the disclosure in U.S. Pat. 5,321,265, and the prior art systems. The prior patent required that the apparatus and methods use only overlapping broad bandpass detectors, while the prior art used neither overlapping nor broadband detectors. The present invention permits the use of a combination of broad and narrow bandpass detectors, as well as the use of both overlapping and non-overlapping sources and detectors; thus, the plurality of detection means may be varied over a greater range of possible combinations and permutations. The increased range of possible detection means allows the sensitivity and specificity of measurements of a given constituent made with this apparatus and method to be greatly enhanced.

The apparatus of the present invention comprises a radiation source, detection means including a plurality of detectors with spectral responses as delineated above, each of which generates an output, processing means which convert some of these outputs into processing input signals, and analysis means generating a signal from these data. The output signal from the analysis means is indicative of the concentration of the constituent of interest. In some embodiments of the invention, the radiation source may be in the form of at least two radiation sources, normally in the near infrared region. In those embodiments, the individual radiation sources are preferably arranged such that each of the radiation sources congruently illuminates the sample. Congruent illumination means that all sources illuminating the sample are completely superimposable in all respects as viewed from the illuminated point (or area) on the sample.

After passing through (or being reflected or emitted from) the sample, the radiation is transmitted to the detection means. Preferably, the detectors in the detection means are arranged in a manner such that the detection means provide congruent measurement of the sample or samples at all the detectors. Congruent measurement indicates that the sample and the detectors are arranged such that the detectors are completely superimposable in all respects as viewed from the observation point (or area) on the sample. The combination of congruent illumination and congruent measurement of the sample insures that all of the detectors examine the same region of the sample through the same solid angle, and thereby minimizes variations due to inhomogeneities in the sample. In a preferred embodiment, the two forms of congruency are used to position the detectors so that the sample is illuminated and viewed through narrowly restricted solid angles, minimizing the effect of wide-angle scattering of the radiation in the tissue on the detector responses.

In some modes of practice of the invention, for example when more than one source is used, a fiber optic bundle may be used to combine the multiple sources for illumination of the sample. Similarly, a fiber optic bundle could be used to provide a path from the sample for transmitted, reflected or emitted radiation to the plurality of detectors. The fibers in the bundle are uniformly distributed in order to assure congruency of the illumination of (or detection from) the sample. Other embodiments of the invention employ beam splitting means to divide or combine the radiation to congruently illuminate or measure the response from the sample or samples. In other embodiments, combinations of beam splitting means and fiber optic means may be employed to assure the congruency of both illumination and detection.

In a particularly useful embodiment of the invention, the sources used to illuminate the sample are coded using electrical or mechanical means, creating, for example, sources with different temporal patterns. These coding patterns appear at the various detectors, attenuated in intensity by their passage through (or reflection from) the sample, but with pattern unchanged. Analysis means employing techniques such as electrical narrow bandpass filters may then be employed as decoding means, permitting the interpretation of the differential response of the various detectors to the various spectral patterns of the sources. This differentiation aids in the interpretation of the overall response of the sample to the illuminating sources. Preferably, at least some of the sources are broadband sources.

The apparatus can further include a sample chamber or similar means for containing or restraining the sample to be measured. The containment means is designed to hold the sample stationary, if necessary, over the time period of the measurement. In a particularly useful embodiment of the invention, the apparatus is provided with at least two sample chambers, holding samples of similar but not identical nature. The same source or combination of sources is used to congruently illuminate each of the samples by the use of beam splitting or fiber optic means, and separate sets of detectors receive the radiation passing through each of the samples. In certain instances, incongruent illumination is used in order to determine perturbations in background. The spectral sensitivity of the separate sets of detectors used may be the same or may be different. In some of the embodiments of the invention, the partial spectral overlap of some of the detectors, along with the spectral non-overlap of at least one detector, is utilized. This spectral pattern is maintained by appropriate choices of the detectors and any associated filtering means. Constituents of the samples to be measured, present in the samples at the same concentration, will appear different depending on the illumination spectrum presented to the samples because of differences in the background properties of the samples. Appropriate analyses of the radiation patterns reaching the separate sets of detection means permit the response of the apparatus to the constituent of interest to be enhanced relative to the response of the apparatus to the background in the samples.

The invention is applicable to transmittance, reflectance, or emittance modes of operation. The term "reflectance", as used herein, means not only classical reflectance measurements but also transflectance or diffuse reflectance measurements where there is some limited surface penetration. Similarly, the term "emittance", as used herein, is used in its broadest aspects and includes fluorescence and any similar form of excited emission. "Transmittance", which is a more accurate term than absorbance in a scattering media, should also be given the broadest possible interpretation.

The methods and apparatus disclosed in the invention are particularly well-suited for the non-invasive measurement of constituents found in human or animal tissues under normal or clinically significant circumstances. Examples of such constituents include but are not limited to glucose, hemoglobin and its variants, pharmaceutical drugs and drugs of abuse, alcohol, and other species. Sample chambers may allow sampling at various sites, including but not limited to the fingers.

In another preferred mode of practice of the invention, the radiation leaving a single measurement site is split among at least two sets of detection means, preferably viewing the measurement site congruently. These detection means have different sets of spectral sensitivities, determined, in a preferred embodiment, by the use of different sets of filtering means in association with the different sets of detectors. In such an embodiment, at least some of the filtering means are individually chosen within each set in order to maintain appropriately broad but differing spectral sensitivities for the detectors. The detector sensitivities may be all overlapping, all non-overlapping, or some combination thereof. When properly chosen, the differing spectral sensitivities of the detector sets will produce different data on the background constituents of the sample and substantially similar data on the constituents of interest. Appropriate analysis of the data generated by the two sets of detection means permit the response of the apparatus to the constituent of interest to be enhanced relative to the response of the apparatus to the background in the sample. In some cases, a black/white luminosity detector, which is responsive to and overlaps the spectral response of all the detectors, is used to provide a reading on the total illumination. A variety of detection means may be used to practice the disclosures of this invention. Preferred detectors having sensitivities appropriate to the invention include detectors based on silicon, on lead selenide, on indium gallium arsenide, germanium, and lead sulfide but other detectors may also be employed.

Outputs from the detectors are processed using techniques which represent another part of the invention. In the simplest form of the invention, the processing of the detector outputs is performed by following the standard methods established for tristimulus colorimetry, in which each output is normalized by dividing it by the sum of all the other outputs. It is to be noted that in the present invention, the processing and combination of the individual detector outputs to provide the detector response is performed, preferably in the hardware, on the direct measurements of radiation intensity received by the individual detectors. This is to be contrasted with the standard methods of spectrophotometry, in which signals are logarithmically transformed into absorbances in accordance with Beer's law prior to subsequent analysis to obtain constituent concentrations. The problem with the latter procedure is that as Beer's law breaks down, i.e., the absorbance is not linearly related to concentration, the information generated by the device degenerates. Note further that the processing used in the present invention provides an improved normalization of the responses, which will aid in the elimination of background interferences.

A further advantage accrues to the mode of data processing disclosed in this invention. The response of the detectors to a "pure" sample, e.g., a sample only containing the constituent of interest, may be described by a multi-dimensional analog of a "color" in the infrared. Analogous to the CIE color description, each constituent will have a specific description in the multi-dimensional coordinate system chosen. The dimensionality of the coordinate system is equal to, or less than, the number of detectors, and the description changes from coordinate system to coordinate system depending on the range and sensitivity of the detectors.

Assuming that all of the signal from all the background including interfering constituents and scattering effects could be segregated into a single background "color", then the signal from a sample containing the constituent of interest in such a background could be described in terms of a specific vector analogous to the hue and chroma values it would have in the visual CIE color description. In a mixture or solution, increasing concentrations of the constituent of interest could be described as having increased brightness (the L-coordinate in CIE Lab space) with no change in the direction of the vector from hue and chroma. If such a segregation were accomplished, the concentration of the constituent of interest in such a mixture or solution could be expressed as a function of a single measured variable in the appropriate coordinate system, i.e., $C=k_0+k_1 f(x)$.

In general, unexpected or unknown interfering constituents may act to prevent complete segregation or discrimination of the detector response to the constituent to be measured from the response to the interfering constituents. However, appropriate choice of the number and spectral sensitivity of the detectors and use of other discriminatory techniques disclosed herein can eliminate effects due to known background components, such as water, hemoglobin, and tissue scattering. When measuring trace constituents such as glucose, the effects of these known background components may be on the order of $10^4$ or more higher than the effect of the desired constituent itself. This segregation can be accomplished by interpolation from one set of detectors to another, because the effects of these dominating background constituents vary smoothly, albeit possibly non-linearly, from wavelength to wavelength. The effects of the trace constituents such as glucose can be seen as offsets on the more global effects of these background components. As a result, the residual signal, e.g., the signal after the effects of the backgroumd components are removed, will have a much higher component due to the trace constituent of interest than if these corrections were not performed. The portion of the residual signal due to the constituent of interest may then be accurately estimated by the analysis means. This is accomplished by characterizing the residual signal as an analog of a location in an n-dimensional space, where n is equal to, or less than, the total number of detectors composing the residual signal.

In most situations, the residual signal is much smaller than the signal due to the known background components. In vector analysis terms, most of the components parallel to the vector direction (or effects) of the constituent of interest are related to concentration. The small signal range implies that the signal due to the constituent of interest can be expected to be substantially linear with concentration.

Elimination of the effects due to known background constituents and scattering reduces the number of calibration steps. Calibration will thus require the estimation of fewer calibration constants than in standard spectrophotometric methods, since spectrophotometric methods must account for known background interference signals in their calibration processes. In the optimal case, the residual signal will, by proper choice of detector number and characteristics, have a "color" that "matches" that of the pure constituent of interest, resulting in the simplest form of calibration.

In another embodiment of the invention, one may employ narrow bandpass detectors such as are used in spectrophotometric apparatus to generate a measurement of radiation intensity as a function of wavelength. This information may then be processed by appropriate processing means to generate similar colorimetric-like information representative of broad features of the sample spectrum and thus provides a method by which standard spectrophotometric apparatus may be adapted to employ the beneficial features of this invention. For example, the output from a plurality of narrow bandpass detectors may be combined to simulate the broadband detection one obtains from the broad bandpass detectors preferred in the present invention and the calorimetric approach can then be used to obtain similar results. This broadband detection is based on the combined properties of the source, the sample and the detectors.

Other aspects of the present invention provide further powerful assistance in the removal of background interferences and the normalization of signals at the detectors. As noted, a black/white luminosity detector, whose spectral response completely overlaps all of the individual detectors, may be included in the apparatus to provide another level of signal normalization.

Similar benefits are obtained from another aspect of the invention, in which a portion of the illuminating radiation is transmitted through a reference material to an additional detector. In one embodiment, the reference material may be placed in the apparatus between the sample and the additional detector by splitting the output from the sample so that a portion of the output goes to the additional detector. This reference material can be a liquid solution containing a high concentration of the constituent of interest, or a particular interfering substance, or be a selected solid material, and thereby reduces the effects of variation of the constituent of interest on the measurement of that constituent in the sample. Inclusion of the reference material in this manner provides an estimate of the response of the detection means to a sample with a zero concentration of the constituent of interest. In a second embodiment, the reference material is chosen to simulate the spectral response of a sample with a zero concentration of the constituent of interest, but with substantially all of the background constituents included. Use of the reference detector in this manner minimizes the effect of many background constituents.

A further highly preferred embodiment of the invention relates to the time scale of the individual measurements. Many spectrophotometric apparatus require as much as one to two minutes to generate all the individual narrow bandpass wavelength measurements required to approximate the entire spectrum of interest. This can be a problem if there are changes in the sample over the time of obtaining the spectrum. By contrast, the present system obtains all of its data substantially simultaneously, generating many individual measurements per second. This permits quantification of changes in the sample measurement due to physiological effects at a slower time scale, such as the change in volume of the sample produced by the arterial pressure pulse, occurring at a frequency of 0.5–3 hertz. By measuring the sample throughout one or a short series of arterial pulses, the apparatus is able to discriminate the signal provided by effects due to the pulse of blood volume introduced from the effects of the steady-state blood volume and those due to the surrounding tissue. This data treatment reduces interference from scattering and interferences from the tissue and provides further opportunities for signal normalization and data discrimination. Additionally, measurements can also be made at a rate that is substantially simultaneous with respect to any time varying instabilities, drifts, or other variations in the characteristics of the apparatus. The effects of such instabilities are thereby minimized.

In another aspect of the invention, the signals are input into an analysis means some of whose components simulate the functions of a neural network. Such a simulation may be performed using electronic hardware or using computer software. The simulation provides a closer approximation to the functions of human color vision. Among the advantages accruing from this aspect of the invention is an increased capability of the apparatus to compensate appropriately for variations in illumination spectra and intensity.

The Drawing and the Detailed Description will more clearly describe the nature and scope of the disclosed invention.

DETAILED DESCRIPTION OF THE INVENTION

The present invention provides methods and apparatus for non-invasive measurement of the concentration of a constituent of interest that interacts with radiation in a selected region of the electromagnetic spectrum, preferably 700–2500 nm. The mode of interaction occurring may, for example, be absorption, reflection, or emission of radiation. Additionally, since such interactions also define the optical properties of objects, this invention in its various embodiments may also be used for measurement of such optical properties.

The apparatus and methods disclosed herein provide improved capabilities for non-invasive concentration measurement under conditions where the classical spectrophotometric systems are inadequate or useless. These capabilities arise from the recognition that such experimental conditions can cause the information obtained by a spectrophotometric system to be unreliably related to the concentration of the constituents of interest.

Complex analysis techniques to decompose the information derived from spectrophotometric methods have been attempted to increase the utility of the data obtained, but these methods usually introduce noise in the data processing and lose information in unexamined regions of the spectrum. Instead, by applying an analog of color perception to concentration measurements, significantly better information relating to concentration can be obtained. The technique is particularly useful in the near infrared region of the spectrum.

Figure 1A:
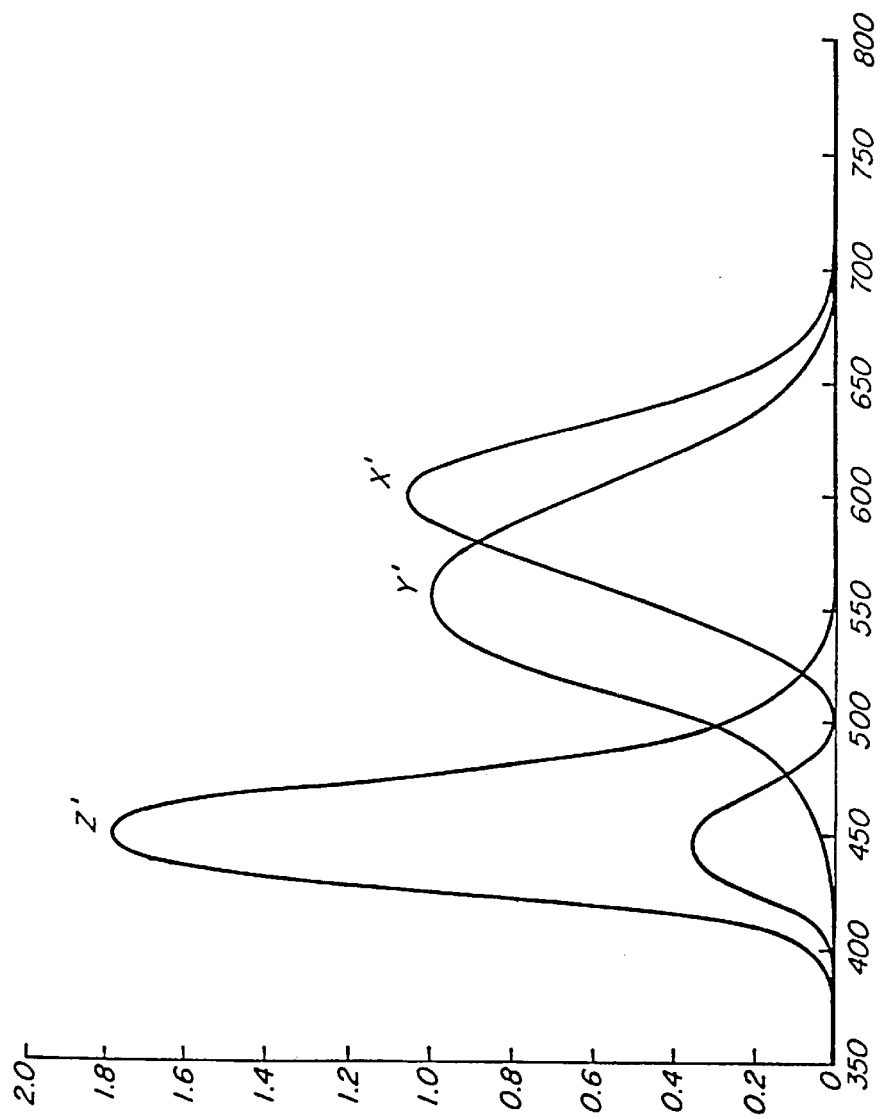
FIG. 1a–c shows three different methods of presenting the color perception spaces for human vision, following the CIE protocols.
Figure 1B:
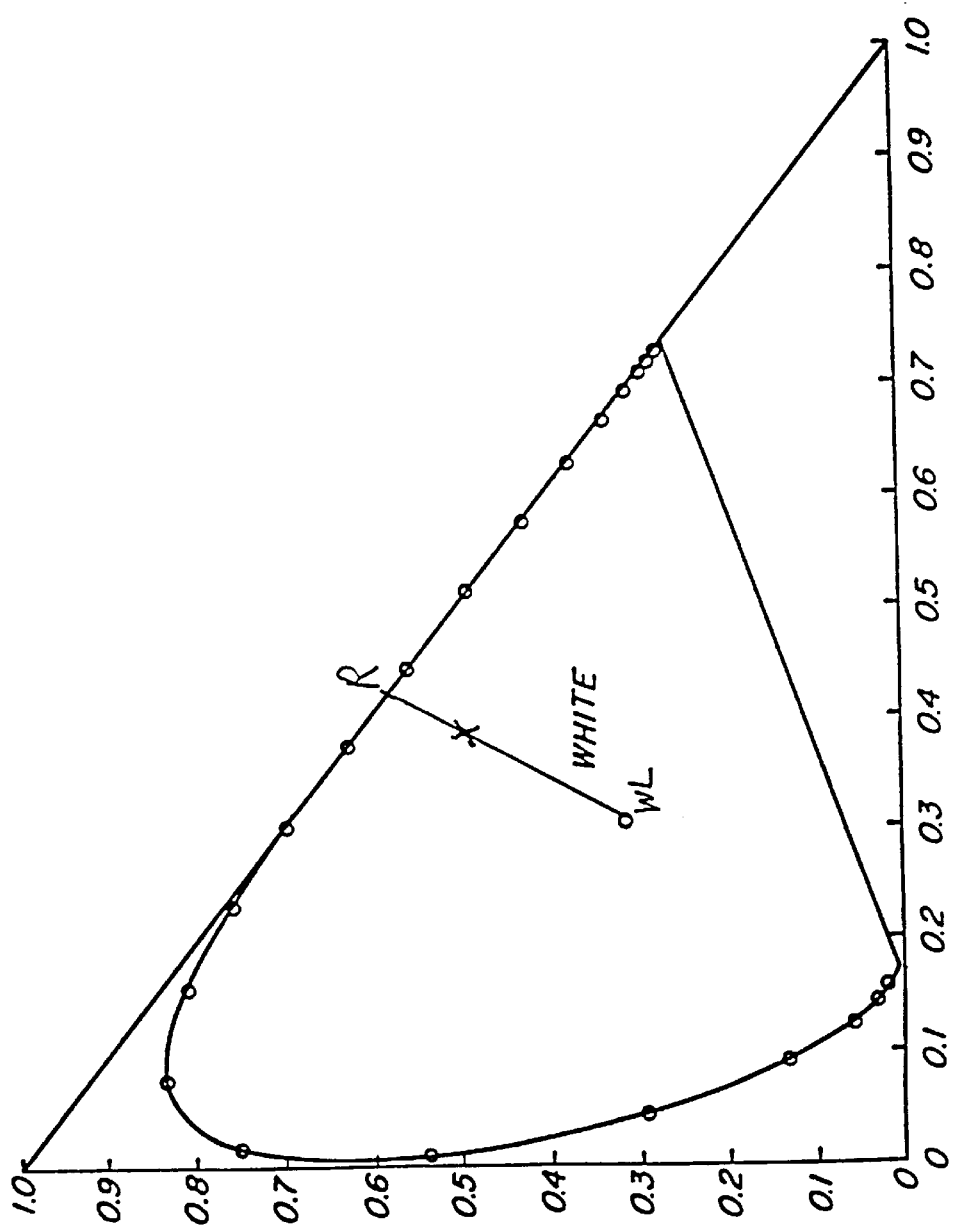
Figure 1C:
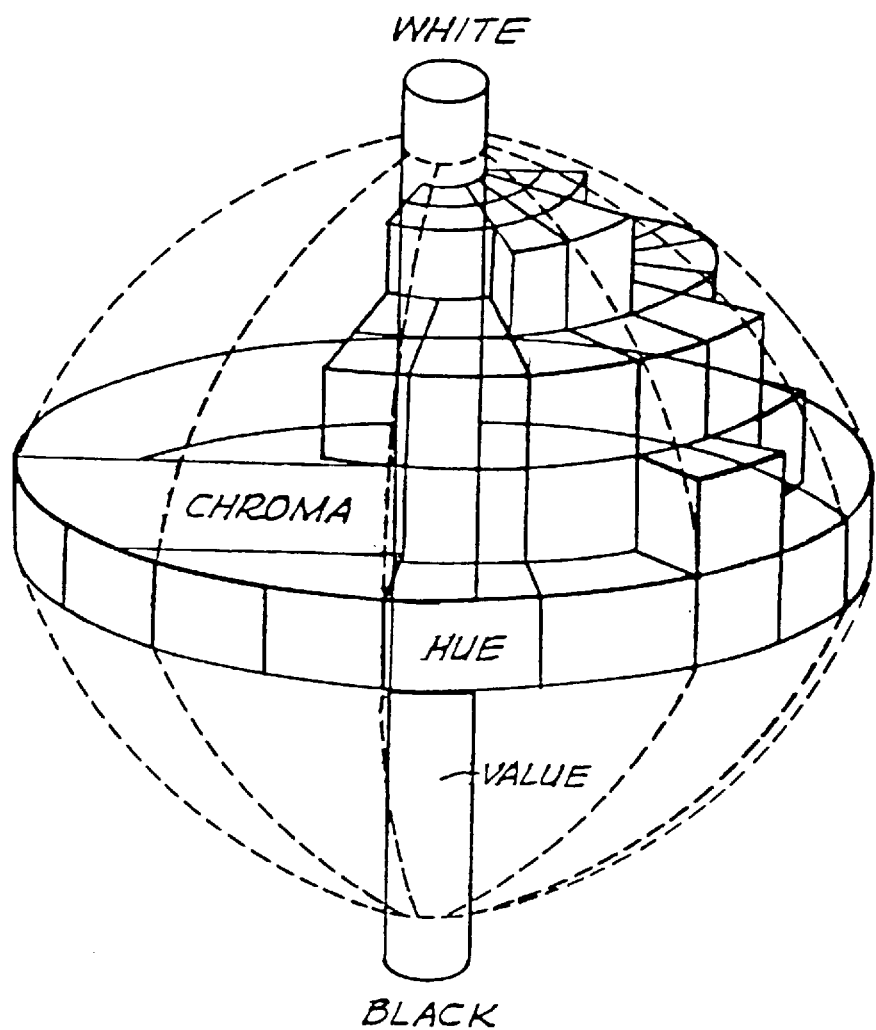

The application of these colorimetric principles to the measurement of concentrations may be understood by referring to FIGS. 1a through 1c, which show different schemes used for interpreting data in classic instrumental colorimetry. FIG. 1a shows the CIE 1931 Standard Observer, which approximates the spectral response of the three types of cones in the human retina. FIG. 1b, called a chromaticity plot, is a convenient two-dimensional representation of the systematic variation of the response of the standard observer of FIG. 1a to monochromatic light of different wavelengths. Each point on the continuous curve in FIG. 1b is plotted as a normalized (X,Y) pair. The pairs of values are obtained from the three response curves in FIG. 1a by dividing the individual response by the sum of the three responses:

$$D=x'+y'+z' \quad X=x'/D \quad Y=y'/D \quad Z=z'/D$$

This normalization procedure completely defines X, Y, and Z. Specification of X and Y values on the two dimensional plot of FIG. 1b specifies Z as well, since the normalization assures that $X+Y+Z=1$. Monochromatic light produces a response falling along the horseshoe shaped curve in FIG. 1b. Using this normalization procedure, monochromatic light falls at the same point along the curve independent of its brightness or intensity, so that the intensity, nominally D, must be specified separately. White light of any intensity falls at the point $X=0.307$, $Y=0.314$, the point designated WL on FIG. 1b.

If the light is not monochromatic, as is the case with light from real objects, the perceived color is described by points within the interior of the curve. The hue or dominant "color" of the object is defined as the perceived color of the monochromatic light which lies at the intersection of the outer curve with a line from the white light point (WL) through the object's location on the chromaticity plot. Line WL-R on FIG. 1b is an example of this type of line and point R indicates the hue. The saturation, also called chroma, of the light from the object is given by the relative distance of the object's location on the plot between the white light point and the horseshoe-shaped curve. The saturation measures the purity of the object color by indicating the required proportion of white light to be mixed with the monochromatic color (corresponding to R on the Figure) to generate the perceived color.

The co-ordinate transformation shown in FIG. 1b makes the Standard Observer curves easier to understand but in practice leaves users with non-linearities in attempting to use it to quantitate perceived colors. Further transformations, such as that shown in FIG. 1c, the so-called CIE Lab space, both minimize those non-linearities and are more easily interpreted by users and have supplanted the chromaticity coordinates in practical usage. For the purposes of this invention, it is important to note that many non-linear transformations of colorimetric data can be applied successfully in the treatment of measurement data intended for different applications.

Figure 2A:
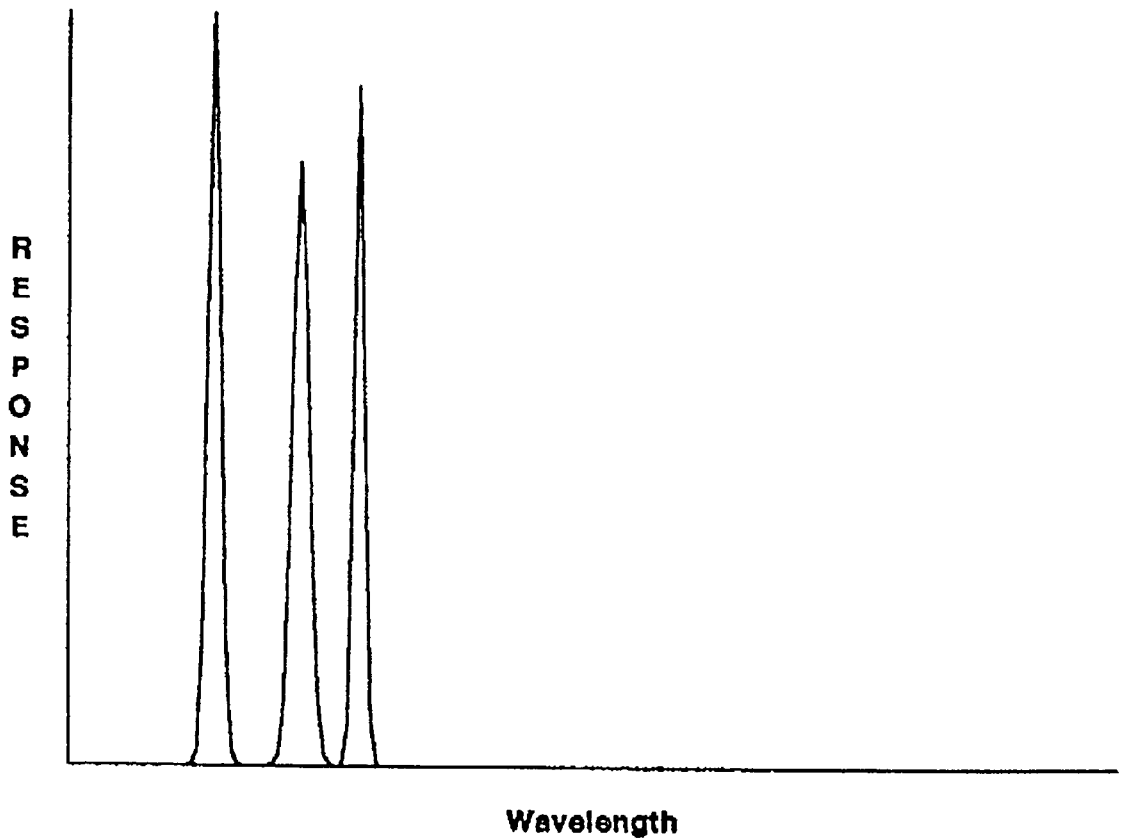
FIG. 2a–f shows the detector spectral output sensitivities for a prior state of the art configuration of spectrophotometer technology compared with a number of different configurations of the invention.
Figure 2B:
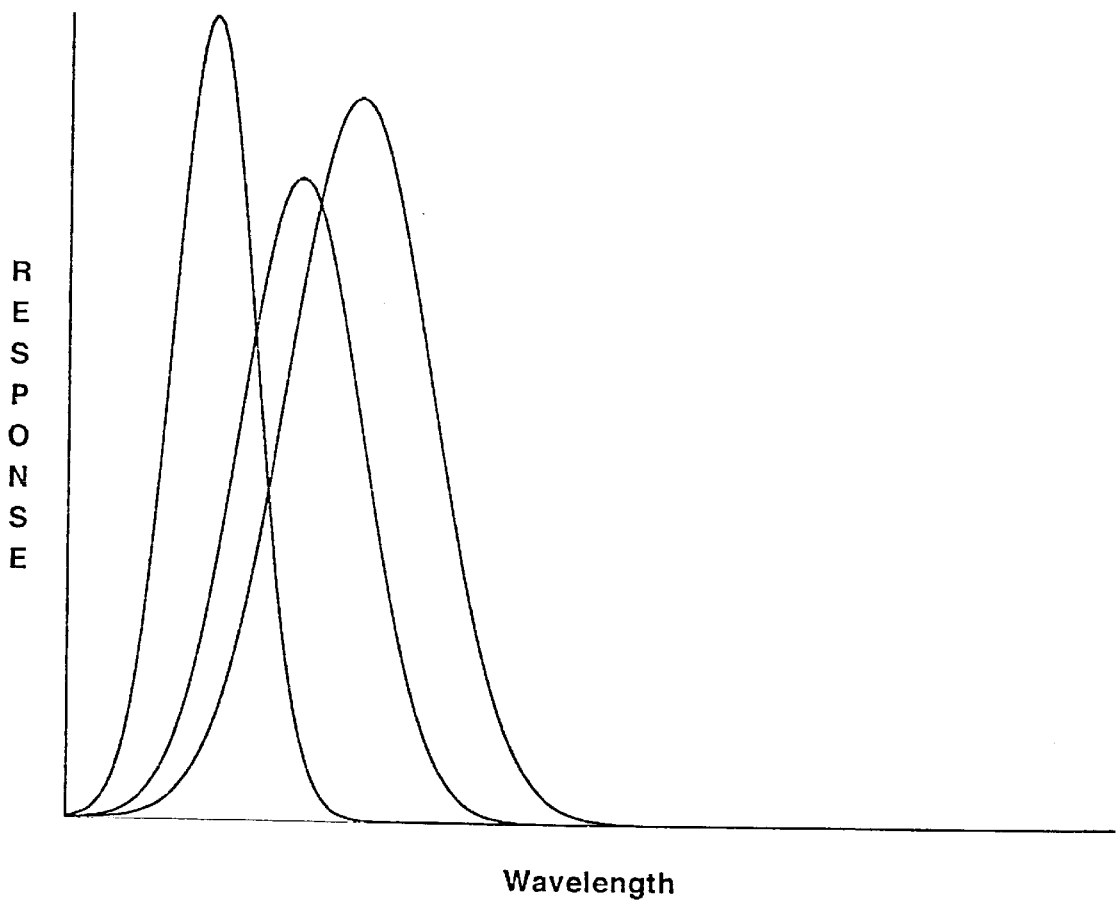
Figure 2C:
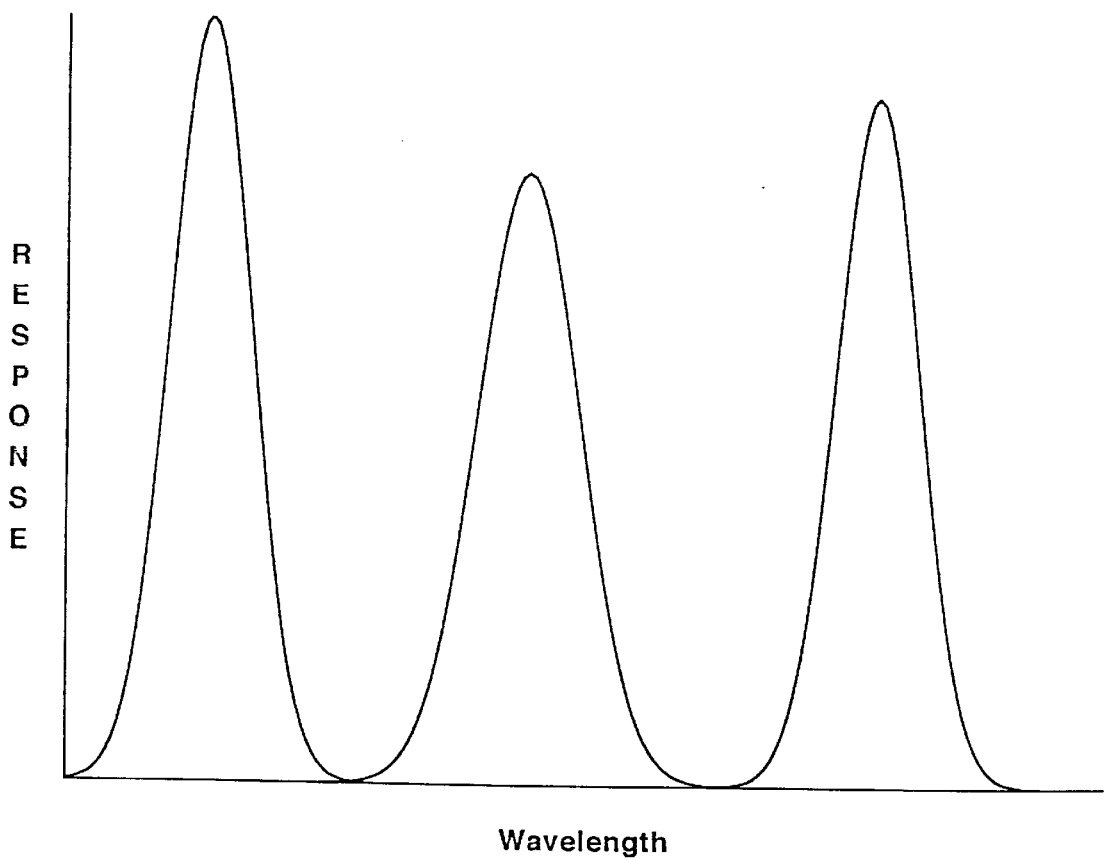
Figure 2D:
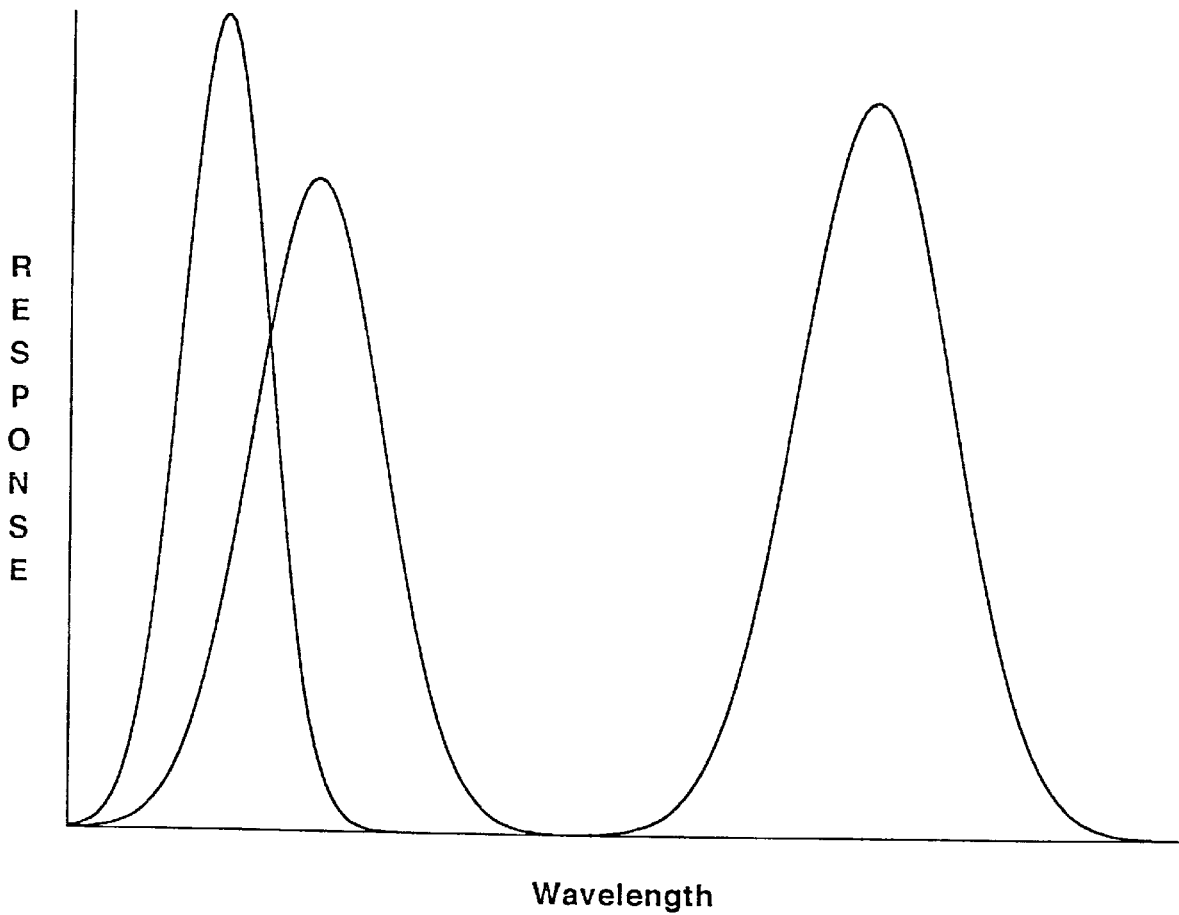
Figure 2E:
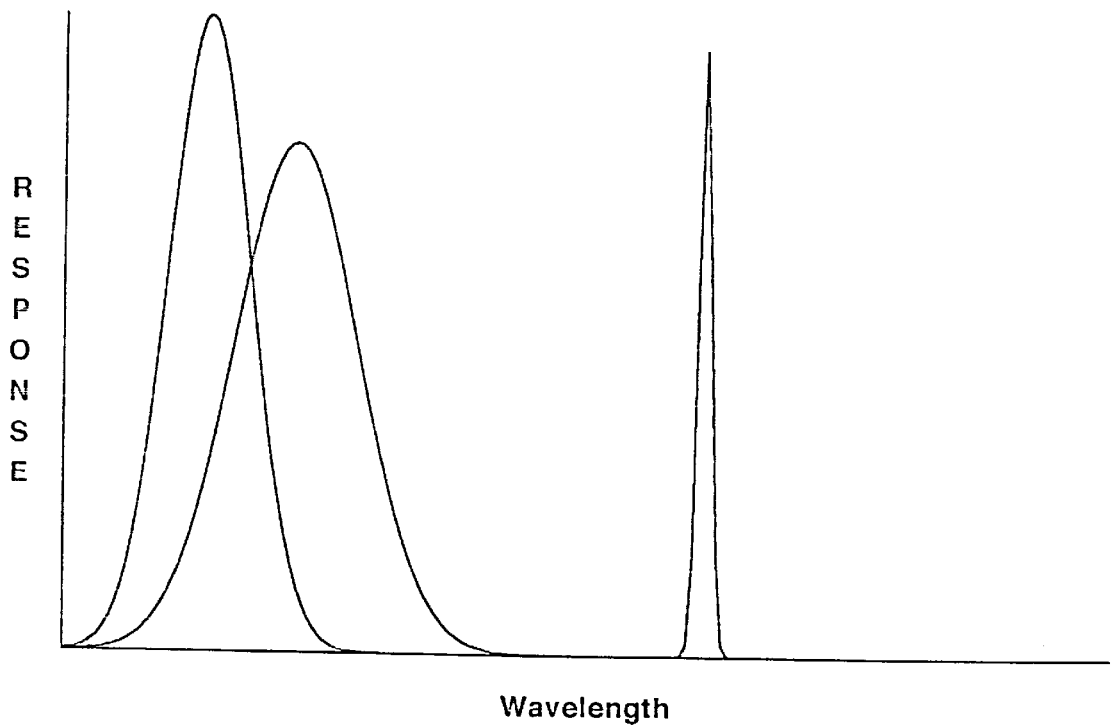
Figure 2F:
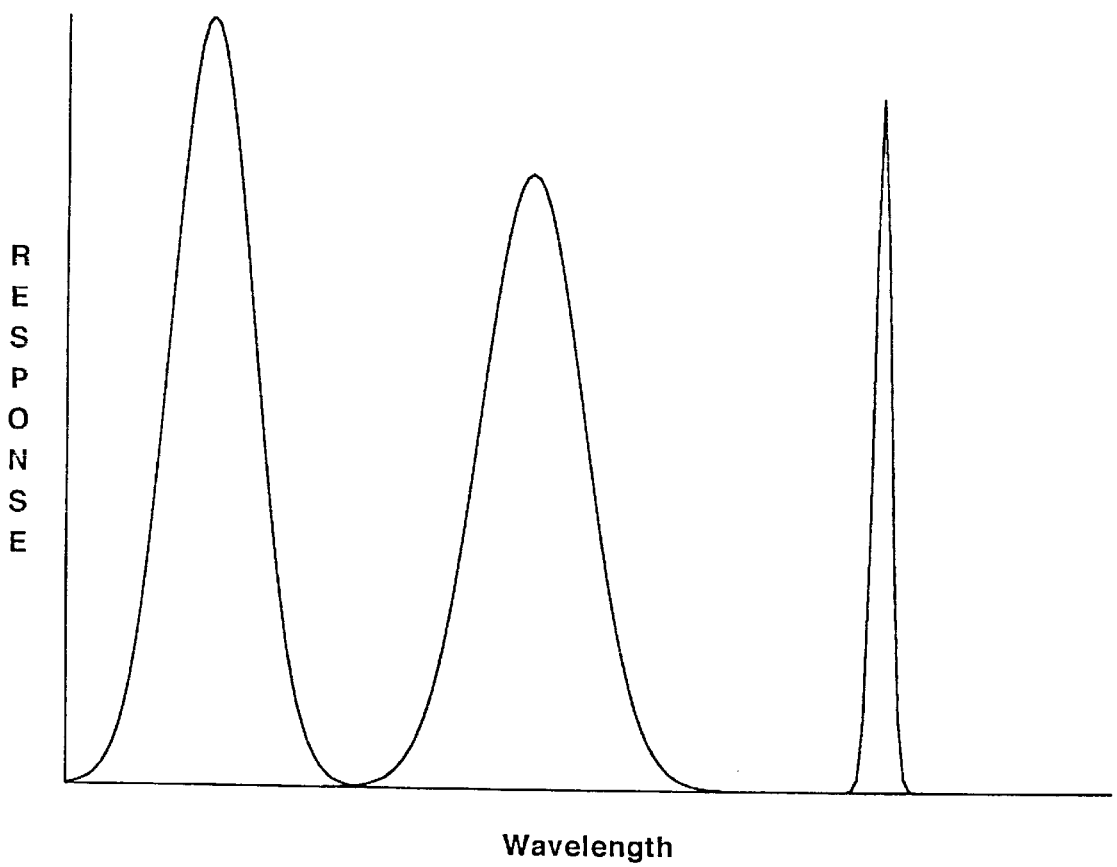

In the present invention, an analog of colorimetric space in the near infrared region of the spectrum is employed. The individual cones of the retina are replaced by a detection means (or several detection means) each formed of a set of n radiation detectors. As in the retina, these detectors preferably have broad, overlapping spectral responses, which are defined by the response of the base detector combined with that of any optical filtering means which may be associated with that detector. However, while the present invention is preferentially practiced by broad bandpass detectors with spectral overlap, non-overlapping detectors, either broadband or narrowband, can be used to replace or supplement as required provided their signal to noise behavior is adequate for the measurement. The breadth of response of the broad bandpass detectors is broad in contrast with spectrophotometric practice, in which detector spectral bandpass is chosen to be as narrow as feasible. For the purposes of this invention, broad bandpass may be taken as broad relative to the halfwidths of one or more relevant sample, constituent, or background spectral features, as that relative breadth is thought to affect linearity and/or specificity in spectrophotometry. Broad bandpass detectors useful in the present invention normally have a bandwidth of at least 50 nm, although in some circumstances, bandwidths as small as 20 nm may be considered broad. FIG. 2a shows the spectral response of a set of all narrow bandwidth detectors, FIG. 2b shows the response of three broadband overlapping detectors such as is shown in U.S. Pat. No. 5,321,265, FIG. 2c shows the response of three broad non-overlapping detectors, FIG. 2d shows the response of three broadband detectors where two overlap and one does not overlap, FIG. 2e shows the response of two overlapping broadband detectors and one non-overlapping narrowband detector, and FIG. 2f shows two broadband detectors and one narrowband detector, with no overlap. As is well understood in the art, many possible detector and filter configurations are feasible that maintain the configurations indicated in FIG. 2 while achieving other purposes insofar as limitation of noise or enhancement of signal is concerned. The constraint on the detector spectral responses shown in FIG. 2 provides substantially greater choice in the configurations of detectors available, and therefore allows improved optimization of the apparatus.

Figure 3:
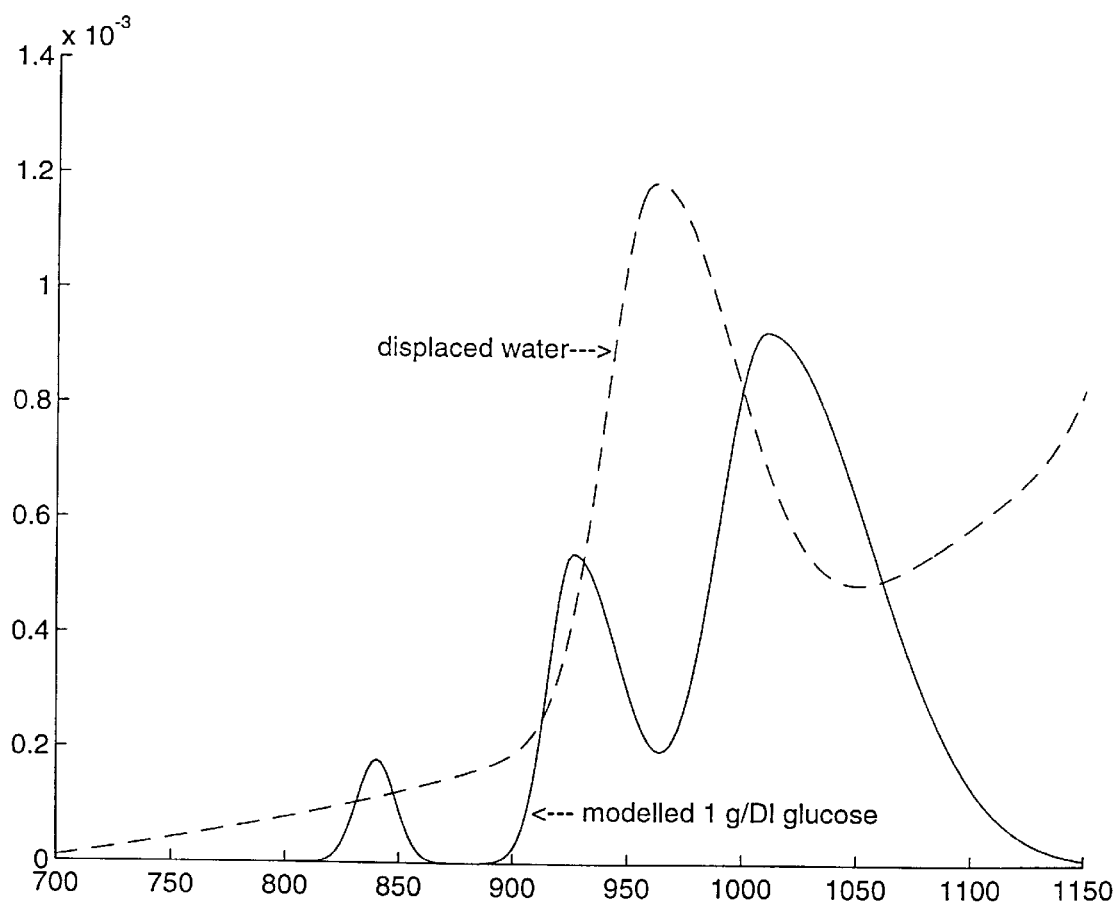
FIG. 3 shows a sample infrared spectrum for water and for an aqueous glucose solution.

Possible arrangements for the spectral sensitivities of the detectors may be understood by referring to FIG. 3, which presents approximate transmission spectra for water and aqueous glucose solutions in the infrared region. The difficulty in obtaining reliable spectra for glucose solutions is well-known and is caused by the small magnitude of the absorbance by glucose in this spectral region and from the non-specific effects on the absorbances and volume as the glucose is combined in solution with the water. The observed changes in the spectrum indicated in FIG. 3 are a combination of all these effects, and serve as only an indication of those changes that might be expected in a non-invasive biological measurement. A rough estimate based upon data in the literature (see, e.g., Koashi et al., U.S. Pat. No. 4,883,953; and Rosenthal, U.S. Pat. No. 5,028,787) suggests that physiological levels of glucose will absorb radiation in this region at approximately 1/2000 the magnitude of the absorbance of physiological concentrations of water. In addition, the effects of other absorbing species, such as proteins, lipoproteins and lipids, as well as scattering, must be accounted for in order to obtain clinically significant data.

Thus, to measure analytes such as glucose in the presence of large amounts of background, the detection means must be configured so as to maximize those changes caused by glucose, while minimizing the effects of changes in other constituents. The apparatus disclosed herein aids in this configuration, compared to the prior art, by allowing more possible configurations of the detector sets. It does so while maintaining the advantages of the calorimetric analog previously disclosed, in that a response (equivalent to a "color") due to glucose throughout the entire spectrum, measured with an optimized weighting function (the chosen co-ordinate space defined by the detector sensitivities), is still made available to the analysis means. In a preferred embodiment, operating on intensity levels, specifically by combining the intensities before any additional mathematical processing occurs, minimizes the problems caused by the deviations from Beer's law. This type of processing and analysis allows the comparison of data from several detection means which can generate information indicative of the concentration of the constituent of interest while rendering the interfering features of the backgrounds from each of the detectors to be less distinct than it is in the individual detectors. Further improvements in accuracy are accomplished by eliminating effects generated by known background components and interfering substances prior to further processing. In a preferred embodiment, the outputs from several detectors are keyed to background effects such as scattering and known interferents such as water and/or hemoglobin, so these can be used to correct for background offsets which leads to more linear results using the background corrected data.

Figure 4:
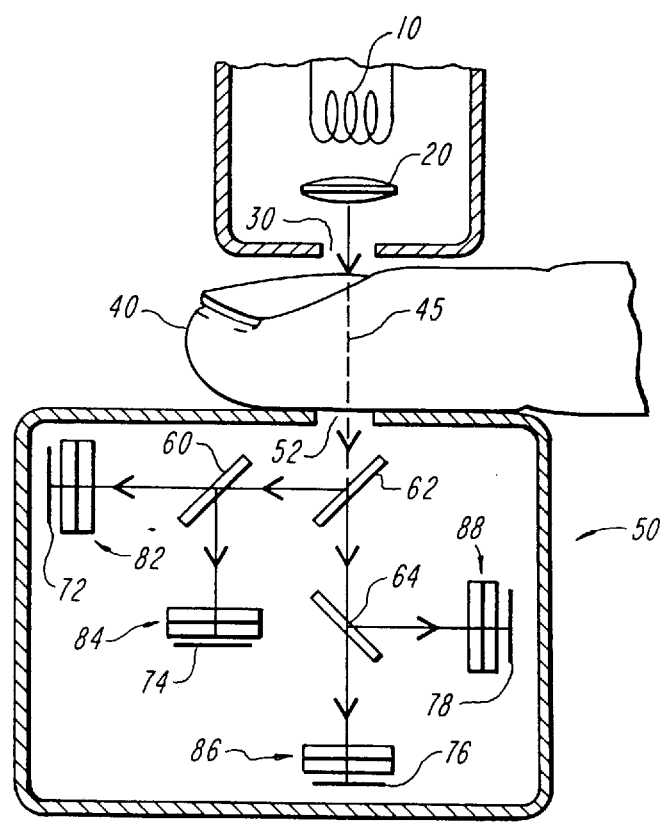
FIG. 4 shows a detailed schematic drawing of one embodiment of the apparatus.

One configuration of apparatus that is particularly useful for the non-invasive measurement of analytes such as glucose in human or animal tissues is illustrated in FIG. 4. This apparatus achieves congruent detection, thereby gaining its advantages. This apparatus has a source of illuminating radiation 10, which preferably generates infrared radiation in the 700–2500 nm range. In some embodiments, source 10 can be replaced by several sources arranged so as to provide congruent illumination. If several sources are used, they can be identical, generate a range of wavelengths, or some combination thereof. Congruent illumination is achieved from multiple sources by the use of reversed beam splitters serving as beam combiners, fiber optic bundles, or the like. If fiber optic bundles are used, they accept the radiation from the different paths and are combined into a fiber optic bundle having randomly spaced fibers which results in a substantially uniform mixture of the radiation from the various sources. Sources 10 are located so that the illumination emitted from the sources and reaching the sample chamber 30 is congruent illumination. The radiation from source 10 is focused by a launch lens 20 through an aperture 30. Aperture 30 leads to sample chamber 40, which is shown having a finger portion 45 therein. If fiber optic bundles are used, they are arranged as is shown in U.S. patent application Ser. No. 130,257.

Sample chamber 40 may, in some advantageous embodiments, be replaced by a plurality of devices for holding similar but not identical sampling sites (such as multiple fingers). In such a case, beam splitting means are employed to insure separately congruent illumination of each of the sampling sites using the same set of sources.

Radiation transmitted or reflected from the sampling site 42 in sampling chamber 40 is directed to the detectors 72, 74 and 76 by beam splitting means 60,62 and 64, or lenses or fiber optic bundles as required. Before reaching the detectors 72, 74 and 76, the radiation is first passed through any required filters 82, 84 and 86. Filters 82–86 are used with detectors 72–76 to provide the requisite wavelength sensitivity. As described previously, any combination of overlapping or non-overlapping, narrowband or broadband, filters can be used. Preferably, at least some of the filters are overlapping broadband filters, which are advantageous in segregating signal components from scattering and known interferents such as hemoglobin and its variants, lipids, and proteins. Although three detectors and filter sets are shown, the number of detectors is not limited and in certain circumstances, having many more detectors may be useful. Detectors having sensitivity to infrared radiation, may be, but are not limited to, silicon, lead selenide, indium gallium arsenide, germanium, and lead sulfide cells.

The spectral properties of filters 82–86, along with the spectral sensitivities of detectors 72–76, combine to produce the spectral response of the detector set or sets. In particularly advantageous embodiments, multiple detector sets and filters are employed to create sets with different spectral responses, optimized for different characteristics of the constituent or constituents of the sample to be measured. These different sets may then be used to detect radiation transmitted through the same sample 30 or through similar but not identical samples. Appropriate comparison of the data generated by these analyses serves to minimize the effect of background relative to the signal produced by the constituent of interest. Using the colorimetric analogy, it may be stated that the apparent color of the constituent of interest will be maintained in the two detector sets, while the apparent colors of background constituents will be different, so that comparison of the data will accentuate the color of interest.

Figure 5:
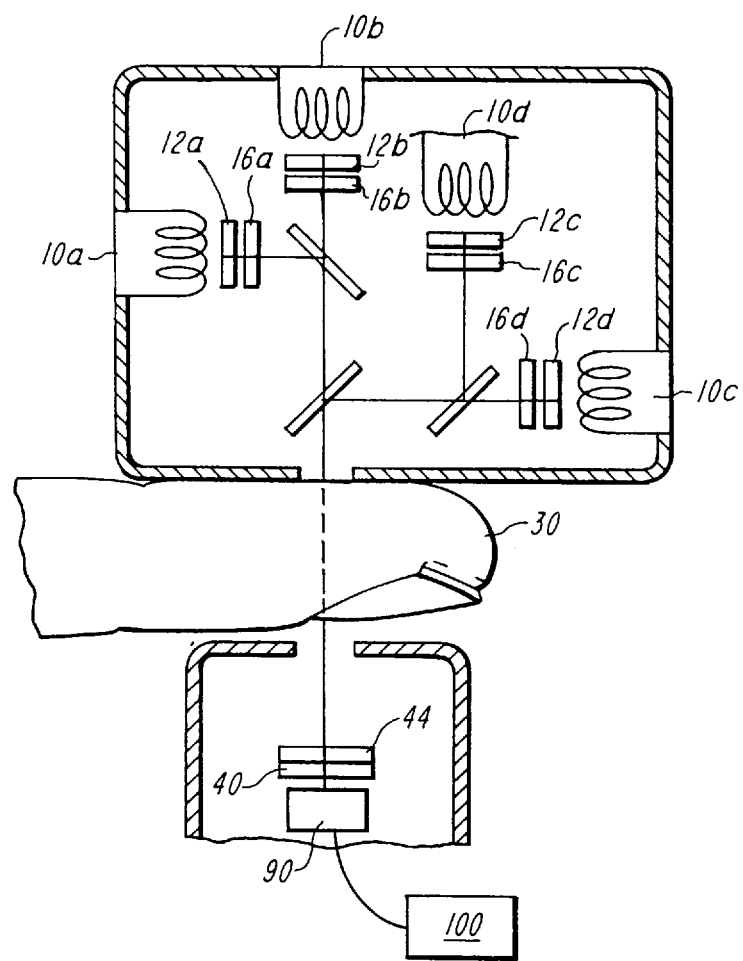
FIG. 5 shows a detailed schematic drawing of another embodiment of the apparatus.

FIG. 5 shows a different variation on the apparatus of the invention. Sources 10a, 10b, 10c, and 10d with emissions including all or part of the 700–2500 nm region, produce the required near infrared radiation. Coding devices 12a, 12b, 12c, and 12d which may be mechanical apertures or electrical means for interrupting the radiation following paths toward the sample and detector, impose distinct temporal patterns on each of the radiation paths employed. This temporal coding allows discrimination of radiation reaching the detector from the intended source from that originating external to the apparatus, as well as allowing the discrimination of illumination from one source relative to that from another source. The radiation from each of radiation sources 10 preferably has an associated filter 16a–d associated therewith to limit the radiation from each source to a particular section of the spectrum. While it is preferable to use at least some broadband overlapping sources, the sources may be broadband or narrowband, overlapping or not.

The radiation from sources 10a–d is transmitted through a sample held in sample chamber 30 and is sent to detector 40. In some circumstances, multiple detectors may be used. Detector 40 normally has a decoder 44 associated therewith which decodes the coded signals and identifies the source of radiation. Decoder 44 typically employs electrical narrow bandpass filters, and allows the signals reaching the detectors to be decoded and transduced for transfer to the processing means. FIG. 5 shows one means of achieving this congruent illumination, using reversed beam splitters, although fiber optics could be used as well.

In another aspect of the invention, an additional beam splitter directs a portion of the source or combined sources to a reference detector, with spectral response overlapping that of all the other detection means. This element of the apparatus aids in the normalization of the signal and calibration of the output by accounting for temporal variations in the source or sources. Another useful embodiment interposes a reference element between beam splitter and reference detector. The reference element may be chosen to have a transmission spectrum similar to that of the constituent of interest at a concentration that is very high compared to that anticipated in operation of the apparatus. The signal from the detector under those circumstances will serve as a stable calibration point useful in calibrating the response of the apparatus. In another useful embodiment, the reference element is chosen to have a transmission spectrum similar to that of the expected background constituents, and the response of the detector to illumination through this reference element can be used to compensate for interferences due to such background constituents.

The basic optics and principles involved using the general approaches described herein are described in further detail in U.S. patent application Ser. No. 130,257 and U.S. patent application Ser. No. 182,572. One major difference between the aforementioned patent applications and the present invention is the possible use of narrowband and non-overlapping detectors. While such detectors are not excluded by the prior applications, the present invention, including the processing techniques described herein, allows optimization of their use.

The outputs from the detectors in any embodiment are then transmitted to processing means 90. Processing means 90 has the capability to process the outputs from the detectors into data streams for analysis by analysis means 100 using a variety of techniques. In one preferred embodiment, some of the outputs are combined before any other processing is performed, according to the model of tristimulus colorimetry, as in the equations presented above. Note that contrary to the typical methodology of spectrophotometry, detector outputs are not logarithmically transformed from intensity to absorbance before this processing step. As discussed earlier, this processing step also serves as a primary mode of data normalization, providing an initial element of normalization and background processing.

In another advantageous embodiment, the outputs from the detectors are processed by processing means 90 at a rate much faster than significant physiological processes affecting the detector outputs and occurring in the sample or samples. Of such processes that affect the detector outputs, the most significant is the change in the blood volume of the tissue occasioned by the arterial blood pressure pulse, also known as the plethysmographic wave. Depending on a variety of physiological factors, these waves can occur at frequencies from 30 to 180 per minute, or 0.5 to 3 cycles per second. Hence, processing means 90 must process the data from the detectors at a rate faster than approximately 20 cycles per second. When this is accomplished, the apparatus is able to effectively separate the signal due to pulsatile changes in blood volume from that due to the steady-state blood volume and from the effectively stationary tissue contributions to the signal. This separation greatly facilitates the measurement of the constituent of interest by reducing background contributions due to averaging of unwanted components.

In still another advantageous embodiment, processing means 90 is constructed in such a manner as to allow compensation for known background constituents prior to further processing. Such compensation may be performed by certain types of hardware or software based neural networks. For example, certain detectors having responses with minimal correlation to the concentration of the constituent of interest may give known outputs which can be strongly correlated to known background and interferent levels. Using the outputs from these detectors, the effects of these background constituents on the outputs of other detectors can be minimized. With such compensation methods, the uncertainty in the response of the apparatus to the constituent of interest is markedly reduced in comparison with apparatus functioning without such compensation. Then, mathematical and statistical techniques known to those skilled in the art such as partial least squares and principal component analysis may function more effectively on the remaining data to separate the response of the apparatus to the constituent of interest from the response to the remaining background constituents, by identifying a projection axis which minimizes the analyte concentration error.

In another preferred embodiment, processing means 90 may be used to combine detector outputs from detectors whose radiation sensitivities have been designed to approximate the effects of the background constituents, including the effects of scattering sites, present within the sample. The resultant data from processing means 90 is then compared with a second set of data generated from a different set of detectors before analysis by analysis means 100. This second set of data is representative of the total signal reaching the detectors. By this method, the effects of scattering and tissue background constituents on the detector responses can be largely compensated for before the analysis means is employed to separate out the effects of the constituent of interest in the blood from those of background constituents and scattering within the blood.

As a further advantage of the invention, the processing means processes the outputs from the detectors in such a manner as to generate parameters representative of broad spectral features of the sample. These broad spectral features may, in preferred embodiments, be analogous to those obtained by tristimulus colorimetry in the visual region of the spectrum. Processing of the data in this manner allows the overall "color" in this portion of the spectrum produced by the interaction of the sources with the sample to be decomposed into its component colors, the colors of the background constituents and the color of the constituent of interest. It is further disclosed that, in the proper coordinate representation of said color, the analogous brightness of said color may be proportional to the concentration of the constituent of interest, in a manner analogous with that occurring in the visual spectrum. This proportionality may provide a great advantage to users of the apparatus in terms of ease and expense of calibration and recalibration of the apparatus.

The foregoing description of the invention is meant to be only exemplary and is not intended to limit the scope of the invention. The invention is defined by the following claims.

What is claimed is:

1. An apparatus for determining, the concentration of a constituent of interest in a sample which has transmittance, emission or reflectance in a selected region of the spectrum comprising:

a radiation source which generates a spectrum of illuminating radiation for illuminating at least a portion of said sample;

detection means in the form of three or more detectors adapted to generate an output, each of said detectors having a spectral response in a portion of said spectrum of illuminating radiation emitted by said radiation source, at least one of said detectors having a broadband spectral response, at least one of said detectors further having an overlap in spectral response with another of said detectors; and analysis means for analyzing said outputs from said detectors to generate a signal indicative of the concentration of said constituent of interest in said sample.

2. The apparatus of claim 1 wherein at least two of said three or more detectors comprise overlapping broadband detectors.

3. The apparatus of claim 1 wherein at least two of said detectors comprise non-overlapping broadband detectors.

4. The apparatus of claim 1 wherein said illuminating radiation comprises infrared radiation between about 700–2500 nm.

5. The apparatus of claim 4 wherein said analysis means generates an output which is an analog of a location in an n-dimensional colorimetric space, where n is equal to, or less than, the number of detectors in said detection means.

6. The apparatus of claim 1 wherein said detection means further comprises a separate black/white luminosity detector which is responsive to and overlaps said spectral response of all of said three or more detectors.

7. The apparatus of claim 1 wherein said analysis means comprises a neural network.

8. The apparatus of claim 1 wherein at least one of said detectors comprises a filter which transmits or reflects a portion of the spectrum of illuminating radiation, said filter acting, at least in part, to generate the spectral response characteristics of said detector.

9. The apparatus of claim 1 wherein at least one of said detectors is formed, at least in part, from a material selected from the group consisting of silicon photocells, lead selenide cells, indium gallium arsenide cells, germanium cells, and lead sulfide cells.

10. The apparatus of claim 1 wherein said sample comprises a portion of an animal body.

11. The apparatus of claim 10 where said animal body is a human body.

12. The apparatus of claim 11 wherein said constituent of interest is an analyte of clinical interest.

13. The apparatus of claim 12 wherein said analyte of clinical interest is selected from the group consisting of glucose, glucose indicating constituents, drugs of abuse, drugs of abuse indicating constituents, alcohol, proteins, lipoproteins, hemoglobin and its variants, cholesterol, and lipids.

14. The apparatus of claim 1 wherein said detectors are located geometrically in said apparatus such that they congruently sample radiation reflected, emitted, or transmitted from said sample.

15. The apparatus of claim 14 further comprising beam splitter means to direct the radiation reflected or transmitted from said sample to said detectors.

16. The apparatus of claim 1 wherein said detection means comprises a fiber optic cable bundle containing a plurality of optical fibers which transmit radiation reflected or transmitted from said sample to said three or more detectors.

17. The apparatus of claim 16 wherein said optical fibers in said bundle have their ends distal from said detectors randomly distributed in said bundle so as to achieve substantially equivalent illumination for each detector from said sample.

18. The apparatus of claim 1 comprising at least a first detection means and a second detection means, each of said detection means having a distinct set of detectors therein.

19. The apparatus of claim 18 wherein at least one of said first and second detection means is arranged to provide incongruent measurement.

20. The apparatus of claim 18 wherein said analysis means comprises means to compare responses from each of said detection means to generate an information signal indicative of the concentration of said constituent of interest while rendering the interfering features of the background from each of said detection means to be less distinct than it is in the response from the individual detection means.

21. The apparatus of claim 18 wherein said first detection means and said second detection means are arranged to obtain radiation from different portions of said sample.

22. The apparatus of claim 1 wherein said analysis means is arranged such that the outputs from said detectors are combined before any additional mathematical processing occurs.

23. The apparatus of claim 22 wherein said analysis means provides mathematical processing of intensity rather than absorbance values.

24. The apparatus of claim 1 wherein said analysis means comprises means to eliminate responses generated from known background components prior to any additional mathematical processing.

25. The apparatus of claim 1 wherein said apparatus comprises interrogation means which collects outputs from said detectors substantially simultaneously.

26. The apparatus of claim 25 wherein said interrogation means collects outputs from said detectors in a sufficiently rapid manner to observe a distinct arterial pulse wave form so as to allow differentiation of constituents of interest in arterial blood, as opposed to venous blood or tissue.

27. The apparatus of claim 1 wherein said detectors are located such that they obtain radiation from said sample only within a restricted solid angle.

28. The apparatus of claim 1 wherein at least a portion of said illuminating radiation is directed through a reference material to an additional detector to generate reference values.

29. The apparatus of claim 1 wherein said radiation source comprises at least two radiation sources.

30. The apparatus of claim 29 wherein said radiation sources are arranged to provide congruent illumination.

31. The apparatus of claim 29 wherein said radiation sources are arranged such that a fiber optic cable bundle containing a plurality of optical fibers can transmit radiation from said radiation sources to said sample.

32. The apparatus of claim 1 wherein at least a portion of said illuminating radiation is directed through a reference material to a detector on a time shared basis to generate reference values.

33. A method for determining the concentration of a constituent of interest in a sample which has transmittance, emittance, or reflectance in a selected region of the spectrum comprising the steps of:

illuminating at least a portion of said sample with a radiation source which generates a spectrum of illuminating radiation;

detecting radiation reflected, emitted, or transmitted by said sample with detection means in the form of three or more detectors adapted to generate an output, each of said detectors having a spectral response in a portion of said spectrum of illuminating radiation emitted by said radiation source;

generating a processing input signal which is responsive to selected aspects of the background of the detection system and the sample, and said constituent of interest, utilizing the output from a broadband detector, or combining the outputs from some of said detectors to simulate broadband detection, at least one of said detectors further having an overlap in spectral response with another of said detectors; and analyzing some of said outputs and said processing input signal with an analysis means which generates a response indicative of the concentration of said constituent of interest in said sample.

34. The method of claim 33 wherein said illuminating radiation comprises infrared radiation between about 700–2500 nm.

35. The method of claim 33 wherein said analysis means generates a response which is an analog of a location in an n-dimensional colorimetric space, where n is equal to, or less than, the number of detectors in said detection means.

36. The method of claim 33 wherein said analysis step is carried out, at least in part, by a neural network.

37. The method of claim 33 further comprising the step of normalizing the intensity of all the radiation transmitted, emitted, or reflected from said sample without regard to wavelength by including in said detection means a black/white luminosity detector which is responsive to and overlaps said spectral response of all of said three or more detectors.

38. The method of claim 33 wherein at least one of said detectors comprises a filter which transmits or reflects a portion of the spectrum of illuminating radiation, said filter acting, at least in part, to generate the spectral response characteristics of said detector.

39. The method of claim 33 wherein at least one of said detectors is a broadband detector.

40. The method of claim 39 wherein at least two of said detectors have overlapping spectral characteristics.

41. The method of claim 39 wherein the outputs of at least said broadband detector forms an input to said processing input signal.

42. The method of claim 33 wherein at least one of said detectors is formed, at least in part, of a material selected from the group consisting of silicon photocells, lead selenide cells, indium gallium arsenide cells, germanium cells, and lead sulfide cells.

43. The method of claim 33 wherein said method is directed at determining the concentration in vivo of an analyte of clinical interest in a portion of a human body and said method is used for non-invasive testing.

44. The method of claim 33 wherein said method is directed at determining the concentration in vitro of an analyte of clinical interest from a human body and said method is used on a fluid or tissue sample removed from said body.

45. The method of claim 44 wherein said analyte of clinical interest is selected from the group consisting of glucose, glucose indicating constituents, drugs of abuse, drugs of abuse indicating constituents, pharmaceuticals, alcohol, proteins, lipoproteins, hemoglobin and its variants, cholesterol, and lipids.

46. The method of claim 33 wherein said detectors are located geometrically relative to said sample such that they congruently sample radiation reflected, emitted, or transmitted from said sample.

47. The method of claim 46 wherein beam splitters are used to direct the radiation reflected, emitted, or transmitted from said sample to said detectors so as to achieve congruent sampling.

48. The method of claim 33 wherein said radiation reflected, emitted, or transmitted from said sample to said detectors is transmitted to said detection means by a fiber optic cable bundle containing a plurality of optical fibers.

49. The method of claim 48 wherein said optical fibers in said bundle have their ends distal from said detectors randomly distributed in said bundle so as to achieve substantially equivalent illumination to each detector from said sample.

50. The method of claim 33 comprising the step of generating distinct outputs from individual detectors in at least a first detection means and a second detection means, each of said detection means having a selected set of detectors therein.

51. The method of claim 50 comprising the step of comparing responses generated from data from each of said detection means to generate information indicative of the concentration of said constituent of interest while rendering the interfering features of the backgrounds from each of said detection means to be less distinct than if only a single detection means was used.

52. The method of claim 51 wherein said first and second detection means obtain radiation transmitted, emitted or reflected from different portions of said sample.

53. The method of claim 50 wherein one of said first and second detectors means is arranged to provide incongruent measurement.

54. The method of claim 33 wherein said outputs and said processing input signals from said detectors are combined before any additional mathematical processing occurs.

55. The method of claim 54 wherein mathematical processing by said analysis means is carried out on intensity rather than absorbance values.

56. The method of claim 54 wherein the analyzing of said outputs and said processing input signals comprises eliminating responses generated from known background components prior to any additional mathematical processing.

57. The method of claim 33 wherein said outputs from each of said detectors are sampled by an interrogation device sufficiently rapidly so as to be substantially simultaneous.

58. The method of claim 57 wherein said interrogation device collects said outputs from said detectors in a sufficiently rapid manner to observe a distinct arterial pulse wave form so as to allow differentiation of constituents of interest in arterial blood.

59. The method of claim 33 wherein radiation from said sample is obtained only from within a restricted solid angle.

60. The method of claim 33 wherein at least a portion of said illuminating radiation is directed through a reference material to an additional detector to generate reference values.

61. The method of claim 33 wherein said illuminating radiation is generated by at least two radiation sources.

62. The method of claim 61 wherein said radiation sources are arranged to provide congruent illumination.

63. The method of claim 61 wherein said radiation sources transmit radiation to said sample through optical fiber bundles and the optical fibers in said bundle have their ends distal from said radiation sources randomly distributed in said bundle so as to achieve substantially equivalent illumination from each of said radiation sources to said sample.

64. The method of claim 33 wherein at least a portion of said illuminating radiation is directed through a reference material to a detector on a time share basis to generate reference values.

* * * * *

UNITED STATES PATENT AND TRADEMARK OFFICE
CERTIFICATE OF CORRECTION

PATENT NO. : 5,818,048
DATED : October 6, 1998
INVENTOR(S) : Lester Sodickson et al.

It is certified that error appears in the above-identified patent and that said Letters Patent is hereby corrected as shown below:

After "[73] Assignee: Optix LP, Jensen Beach, Fla." please insert

--[*] Notice:  The term of this patent shall not extend beyond the expiration date of Pat. No. 5,321,265--

Signed and Sealed this

Twentieth Day of June, 2000

Attest:

Q. TODD DICKINSON

*Attesting Officer*    *Director of Patents and Trademarks*